(12) United States Patent
Kawale et al.

(10) Patent No.: US 10,064,826 B2
(45) Date of Patent: Sep. 4, 2018

(54) DIRECT COMPRESSION AND DRY GRANULATION PROCESSES FOR PREPARING CARGLUMIC ACID TABLETS HAVING LESS IMPURITIES THAN THOSE PRODUCED BY WET GRANULATION PROCESS

(71) Applicants: Sanjay Rangnathrao Kawale, Maharashtra (IN); Mahendra R. Patel, Milltown, NJ (US)

(72) Inventors: Sanjay Rangnathrao Kawale, Maharashtra (IN); Mahendra R. Patel, Milltown, NJ (US)

(73) Assignee: Navinta, LLC, Ewing, NJ (US)

( * ) Notice: Subject to any disclaimer, the term of this patent is extended or adjusted under 35 U.S.C. 154(b) by 298 days.

(21) Appl. No.: 14/213,000

(22) Filed: Mar. 14, 2014

(65) Prior Publication Data
US 2014/0275260 A1 Sep. 18, 2014

Related U.S. Application Data

(60) Provisional application No. 61/794,897, filed on Mar. 15, 2013.

(51) Int. Cl.
*A61K 9/20* (2006.01)
*A61K 31/194* (2006.01)
*A61K 31/198* (2006.01)

(52) U.S. Cl.
CPC .......... *A61K 9/2095* (2013.01); *A61K 9/2054* (2013.01); *A61K 31/194* (2013.01); *A61K 31/198* (2013.01)

(58) Field of Classification Search
CPC .. A61K 9/2054; A61K 9/2095; A61K 31/194; A61K 31/198
USPC ................... 514/566; 424/400, 464
See application file for complete search history.

(56) References Cited

U.S. PATENT DOCUMENTS

| | | | | |
|---|---|---|---|---|
| 7,927,613 B2* | 4/2011 | Almarsson | ............ | A61K 9/145 424/400 |
| 2001/0014352 A1* | 8/2001 | Batra | ................... | A61K 9/2018 424/464 |
| 2006/0193914 A1* | 8/2006 | Ashworth | ............ | A61K 9/2031 424/469 |
| 2009/0202634 A1* | 8/2009 | Jans | ..................... | A61K 9/2018 424/468 |
| 2012/0045506 A1* | 2/2012 | Baer | .................... | A61K 9/5078 424/452 |
| 2015/0374630 A1* | 12/2015 | Arkenau Maric | ... | A61K 9/2031 424/465 |

FOREIGN PATENT DOCUMENTS

| | | |
|---|---|---|
| WO | 2009092601 A1 | 7/2009 |
| WO | 2010105673 A1 | 9/2010 |

OTHER PUBLICATIONS

EMA (European Medicines Agency, Scientific Discussion for Carbaglu (EMEA 2004), 19 pages.*
FDA (Center for Drug Evaluation and Research, Application No. 22-562, Clinical Pharmacology and Biopharmaceutics Review(s), Carbaglu (Carglumic Acid) [Retrieved from internet <URL: http://www.accessdata.fda.gov/drugsatfda_docs/nda/2010/022562s000clinpharmr.pdf >], submission date Jun. 18, 2009, 43 pages).*
Remington (Remington's Pharmaceutical Sciences, Chapter 45, Oral Solid Dosage Forms (2005), excerpt, pp. 889-914, 928 (32 pages total)).*
Remington Dissolution (Remington's Pharmaceutical Sciences (2005), Chapter 35: Dissolution, pp. 672-688 (22 pages total)).*
Gohel (A review of co-processed directly compressible excipients, J. Pharm Pharmaceut Sci (Apr. 16, 2005) 8 (1): 76-93; 18 pages total).*
Chowdary et al., Recent Research on Co-Processed Excipients for Direct Compression—A Review, Pharmacie Globale, International Journal of Comprehensive Pharmacy (IJCP), (Available on-line Feb. 5, 2013), 04 (02): 1-5 (6 pages total).*
Nayak et al., Journal of Pharmaceutical Education & Research (J Pharm Educ Res) (Jun. 2011) 2(1): 21-34 (15 pages total).*
Sandri et al., Review Article: Differentiating Factors between Oral Fast-Dissolving Technologies, American Journal of Drug Delivery (Am J Drug Deliv) (2006) 4 (4): 249-262 (15 pages).*
EMA, Annex I, Summary of Product Characteristics (cited in EMA reference already of record), [Retrieved from internet <URL: http://www.ema.europa.eu/docs/en_GB/document_library/EPAR_-_Product_Information/human/000461/WC500021584.pdf >], [Retrieved Sep. 25, 2017], 23 pages.).*
J. Häberle, Carglumsäure, Arzneimittel-Therapie-Kritik (2006) Series 4, pp. 167-169; original document (3 pages) + translation (14 pages) (total 17 pages).*
Min Li, Organic Chemistry of Drug Degradation, Chap. 9, Sec. 9.13: Impact of Manufacturing Process on Drug Degradation (2012), 287 pages. (excerpt from p. 273 in action).*
Memorial Sloan Kettering Cancer Center (MSKCC), Patient and Caregiver Education, Carglumic Acid, [Retrieved from internet <URL: https://www.mskcc.org/cancer-care/patient-education/carglumic-acid-01 >], (last reviewed date: Dec. 21, 2016), 5 pages.*
Dilip Parikh, How to Optimize Fluid Bed Processing Technology: Part of the Expertise in Pharmaceutical Process Technology Series (Academic Press, Apr. 4, 2017), 210 pages. (excerpt from p. 98 in action).*

(Continued)

*Primary Examiner* — Ernst V Arnold
*Assistant Examiner* — Miriam A Levin
(74) *Attorney, Agent, or Firm* — St. Onge Steward Johnston & Reens LLC

(57) ABSTRACT

The invention provides a process for preparing stable, high API content, solid pharmaceutical dosage forms by direct compression or dry granulation, characterized in that the pharmaceutical tablets rapidly disintegrate in water or other aqueous solutions to produce a clear or almost clear solution. Also provided is a pharmaceutical carglumic acid tablet, which has improved manufacturing, dissolution, and stability properties, and is less expensive to produce, compared to the equivalent commercial product.

9 Claims, No Drawings

(56) References Cited

OTHER PUBLICATIONS

Annex I (EMA Annex I, Summary of Product Characteristics, 9 pages; document provided as Exhibit 2 to Applicant's Remarks of Dec. 28, 2017) (Year: 2017).*
Chemistry Reviews (Center for Drug Evaluation and Research, Application No. 22-562, Chemistry Review(s), (with Memorandum dated Mar. 16, 2010), 19 pages (provided as Exhibit 3 with Applicant's Remarks of Dec. 28, 2017)) (Year: 2010).*
Remington's Pharmaceutical Sciences, 15th Ed., Mack Publishing Co., Easton, Pa., pp. 1576-1598 (1975).
European Search Report Application No. EP 14 16 0221 Completed: Jun. 10, 2014; dated Jun. 20, 2014 5 pages.

* cited by examiner

DIRECT COMPRESSION AND DRY GRANULATION PROCESSES FOR PREPARING CARGLUMIC ACID TABLETS HAVING LESS IMPURITIES THAN THOSE PRODUCED BY WET GRANULATION PROCESS

FIELD OF THE INVENTION

The invention relates to pharmaceutical formulations and processes. More particularly, the invention relates to stable, fast dissolving, solid pharmaceutical formulations containing a high dosage of active pharmaceutical compounds prepared by direct compression or dry granulation process.

BACKGROUND OF THE INVENTION

Tablets and capsules are among the most frequently employed drug dosage forms for delivering active pharmaceutical ingredients ("APIs"). This is because these dosage forms allow for an accurate and easy administration of APIs. Furthermore, handling and packaging, shelf life, and stability of these preparations are generally easier and better than those of other formulations.

To manufacture tablets and capsules, a solid bulk of granulate mass is typically formed by using one of two processes, wet granulation and or dry granulation, and the granulate mass is then compressed into tablets or filled into capsules. Tablets may also be manufactured using direct compression. See, Remington's Pharmaceutical Sciences, 15th Ed., Mack Publishing Co., Easton, Pa., pages 1576-1598 (1975).

In wet granulation, components are mixed and granulated using a wet binder. The wet granulates are then sieved, dried and optionally ground prior to being compressed into tablets or filled into capsules. Wet granulation is used extensively in the pharmaceutical industry although it has proven to be a difficult method, mainly because the liquids needed in the granule may have an adverse effect on the characteristics of the APIs and the stability of the tablets and capsules. For instance, variations in the moisture content of starch used in the manufacturing process may cause the tablets and capsules too hygroscopic or having a reduced shelf life.

Dry granulation is a method of controlled crushing of precompacted powders by either slugging or passing the material between two counter-rotating rolls. Typically, powdered components are mixed prior to being densified by passing the material between two counter-rotating rolls to yield hard slugs, which are then ground and sieved before final production to form tablets or capsules. Substantially no liquids are used in dry granulation. As such, the issues related to wet granulation are avoided. However, dry granulation has not been widely used because of the challenges in producing desired granules as well as managing granulated material in the manufacturing process.

Direct compression requires two principal steps: i.e., mixing the ingredients and compressing the mixture into tablets. Direct compression is considered to be the simplest and the most economical process for producing tablets. However, it may only be applied to a relatively small number of substances that do not need granulation before tableting. Moreover, it is a challenge to find a formulation having an optimal combination of APIs and excipients such that, after mixing, they exhibit desired compressibility, homogeneity and flow-ability for direct compression. Consequently, direct compression has not been widely used in the drug manufacturing processes.

Depending on how APIs are processed into tablets, the physical properties, drug release pattern, and stability of the tablets may be different. For dry granulation and direct compression processes, a small change in drug compositions, or even a change in the order of mixing the components of the same drug composition, may cause segregation and flow-ability problems during the processes, and affect the dissolution and stability profiles of the tablets.

For certain medications, it is required that tablets providing a high dosage of APIs. It is also required that such tablets have fast dissolving immediate release properties. Fast dissolving immediate release properties refer to that the tablet will dissolve in water or aqueous solutions or upon oral administration within a few minutes, preferably within seconds, to produce a clear or almost clear solution.

Fast dissolving immediate release tablets are not easy to manufacture and generally not very stable. Wet granulation is currently the primary method for preparing fast dissolving immediate release tablets. But this method is not ideal because APIs and excipients of fast dissolving immediate release tablets are typically hygroscopic. Consequently, problems such as punch filming, picking and sticking during granulation and compression often occur, which makes the manufacturing processes complicated and time consuming. Making high dosage strength tablets that have fast dissolving immediate release properties are ever more challenging because less excipients are used in the drug compositions, which make it harder to achieve the desired compressibility, homogeneity and flow-ability.

One high dose, fast dissolving immediate release pharmaceutical drug is CARBAGLU tablet, an orphan drug indicated as an adjunctive therapy for the treatment of acute hyperammonemia and for maintenance therapy for chronic hyperammonemia, due to patients' deficiency of the hepatic enzyme N-acetylglutamate synthase (NAGS). In its drug package insert, CARBAGLU tablet is presented as fast dissolving tablet containing 200 mg of (2S)-2-(carbamoylamino)pentanedioic acid (also known as carglumic acid) as an active compound. It is instructed that that CARBAGLU tablet must be dissolved in 2.5 mL of water and administrated immediately to a patient either orally or through a nasogastric tube. CARBAGLU tablet cannot be swallowed whole or crushed. Otherwise it may cause serious adverse effects to the brain or even cause death. Therefore, it is important that CARBAGLU tablet is fast dissolving upon contact with water so that all of carglumic acid in the tablet can be released and dissolved in water.

CARBAGLU tablet is supplied by Orphan Europe SARL, Paris, France. Scientific discussion of European Public assessment reports (©EMEA 2004) discloses that CARBAGLU tablet is manufactured by conventional high shear wet granulation and oven drying process followed by compression to form tablets. The tablets are packed, together with a desiccant unit, in a polypropylene container, which is closed with a screwed polyethylene cap and stored in a refrigerator until use.

CARBAGLU tablet manufactured by the wet granulation and oven drying process suffers from several shortcomings. First, the CARBAGLU tablet prepared by the process is not very stable. This is probably due to the oven drying step in which carglumic acid and the excipients are subjected to a high temperature. As a result, CARBAGLU tablet is more prone to degradation. According to the package label, unopened CARBAGLU bottles should be tightly closed and stored in a refrigerator at 2-8° C. (36-46° F.). After first opening of a bottle, the bottle must be stored at a temperature above the refrigerated temperature 2-8° C. (36-46° F.) but below 30° C. (86° F.). Any unused tablets in the bottle must be discarded after one month from the first opening. Second, as with most of wet granulation processes, the problems such as sticking to the dies and rollers during the preparation of tablets may occur. Such problems are aggravated by the fact that carglumic acid is highly hygroscopic and that a high content of carglumic acid is contained in CARBAGLU tablet. Because CARBAGLU tablet is only manufactured by Orphan Europe SARL in Europe, transporting CARBAGLU tablet to the hospitals and pharmacies in the United States is very cumbersome because the stringent, low temperature requirement for storing and transporting CARBAGLU bottles must be followed during the entire importation.

The recommended initial dose for acute hyperammonemia is 100 mg/kg/day to 250 mg/kg/day. Thus, for a 70 kg patient, the daily dose will be 7,000 mg/day (35 pills/day) to 17,500 mg/day (87.5 pills/day), which translates to a medical bill of $200,000 to $400,000 per month. Typically patients suffered from deficiency of the hepatic enzyme NAGS need to take a maintenance dose of CARBAGLU tablet for life after the initial treatment of acute hyperammonemia.

Thus, there exists a need for a cost effective process for manufacturing CARBAGLU tablet. There is also a need for CARBAGLU tablet or a generic version thereof that has an improved dissolution profile and an improved stability.

It is an object of the invention to provide a simpler and more economical process for producing pharmaceutical drugs in solid dosage forms compared to conventional available process, i.e., wet granulation.

It is another object of the invention to provide a drug formulation that will yield a stable, preferably high drug content, and/or rapidly water dissolving immediate release solid dosage form.

It is a further object of this invention to provide a generic carglumic acid tablet which has improved manufacturing, dissolution, and stability properties, and is less expensive to produce, compared to the equivalent commercial product, CARBAGLU.

SUMMARY OF THE INVENTION

In one aspect, the present invention provides an improved formulation for preparing a pharmaceutical composition of a high dosage of API by direct compression or dry granulation. In another aspect, the present invention provides pharmaceutical dosage forms prepared by the improved formulation. The dosage forms are solid tablets or capsules having a high drug content, which will immediately release the API contained therein upon contact with water, other liquids, or upon oral administration.

According to one embodiment, the present application provides a pharmaceutically acceptable carglumic acid formulation which comprises about 30% w/w to about 50% w/w of carglumic acid, about 40% w/w to about 60% w/w of acellulosic filler, and at least one lubricant, wherein no solvent or water is added or used in the formulation or process.

Preferably, the at least one lubricant is sodium stearyl fumarate, and the cellulosic filler is selected from the group consisting of microcrystalline cellulose, hydroxypropyl methyl cellulose, croscarmellose sodium, silicified microcrystalline cellulose, carboxymethylcellulose, methylcellulose, powdered cellulose, hydroxyethyl cellulose, and combinations thereof. More preferably, the cellulosic filler consists of microcrystalline cellulose and hydroxypropyl methyl cellulose.

The above inventive formulation may further comprise a surfactant, a glidant, a disintegrant, or combinations thereof. Preferably, the glide is colloidal silicon dioxide, the surfactant is sodium lauryl sulfate, and the disintegrant is croscarmellose sodium. In a preferred embodiment, the inventive formulation has a pH greater than 3.5.

The inventive formulation may utilize a dry granulation process or a direct compression process. The dosage forms of the inventive formulation may be either tablets or capsules. In a preferred embodiment, the inventive formulation provides drug dosage forms which exhibit less than 0.1% total impurities after storage for 6 months at room temperature.

According to another embodiment, the present application provides a process for preparing pharmaceutical carglumic acid solid dosage forms comprising the steps of:
(1) mixing a composition comprising about 30 w/w % to about 50 w/w % of carglumic acid and about 40% w/w to about 60% w/w of a cellulosic filler to form a blend,
(2) mixing the blend from Step (1) with a lubricant, and
(3) forming a solid dosage form from the blend from Step (2),
wherein substantially no solvent or water is added in the process.

Prior to mixing the components in Steps (1), and (2), the components of each step may be sieved to obtain a desired particle size of each component, preferably through a 30 Mesh or smaller screen. Optionally, the components may be ground prior to the sieving step. The components may include carglumic acid, the cellulosic filler, the lubricant, and optionally a disintegrant and a surfactant.

According to yet another embodiment, the blend from Step (1) is densified by either slugging or passing the material between two counter-rotating rollers, the resulting densified composition is broken by a suitable milling technique following by sieving to collect a consistent particle size of the composition before proceeding to Step (2).

According to yet another embodiment, Step (2) is comprised of two steps: (2a) mixing the blend from Step (1) with a glidant and a surfactant; and (2b) mixing the blend from Step (2a) with the lubricant.

The inventive process of the present invention is particularly suitable for making hygroscopic drug tablets and capsules because it eliminates water from the process. The inventive method has a good compatibility with acidic and basic APIs. A suitable API is carglumic acid.

The inventive process can be used to prepare drug tablets and capsules having different dosage levels of APIs. A suitable dosage range is from about 100 mg to about 800 mg API/dosage unit, preferably from about 200 mg to about 500 mg API/dosage unit, and more preferably about 200 mg API/dosage unit.

The solid dosage units prepared by the inventive processes may disintegrate within a short period of time, after oral administration or upon contact with water or an aqueous solution, thereby allowing immediate release of the API. Moreover, the solid dosage forms prepared by the inventive processes may exhibit an improved stability.

According to a further embodiment, the present application provides a process for preparing a pharmaceutically acceptable carglumic acid direct compression tablet or capsule comprising the steps of:
(1) dry mixing a composition consisting essentially of
(a) at least one active pharmaceutical ingredient in an amount of from about 30.0% to about 70.0%, preferably, about 40%, (b) microcrystalline cellulose in an amount of from about 30.0% to about 75.0%, preferably about 52.5%,
(c) croscarmellose sodium in an amount of from about 2% to about 8%, preferably about 5.0%, and
(d) hydroxypropylmethyl cellulose in an amount of from about 0.3% to about 2.0%, preferably about 1.0%, by weight of the tablet;

(2) dry mixing the dry-mix blend from Step (1) with anhydrous colloidal silicon dioxide in an amount of from about 0.1% to about 1.0%, preferably about 0.3%, and sodium lauryl sulfate in an amount of from about 0.05% w/w to about 0.5%, preferably about 0.2%, by weight of the tablet;

(3) dry mixing the dry-mix blend from Step (2) with sodium stearyl fumarate in an amount of from about 0.5% to about 2.5%, preferably about 1.0%, by weight of the tablet; and (4) compressing the dry-mix blend from Step (3) to form a compressed tablet, or filling the dry-mix blend from Step (3) to capsules.

Using the inventive preparation methods, the present invention provides a generic carglumic acid tablet which has improved manufacturing, dissolution, and stability properties, compared to the equivalent commercial product, CARBAGLU tablet. The pharmaceutical carglumic acid tablet made by the invention may disintegrate within 20 seconds upon contact with water. Moreover, it has an improved stability at room temperature compared to the commercial product, CARBAGLU tablet.

DETAILED DESCRIPTION OF THE INVENTION

Unless otherwise defined, all technical and scientific terms used herein have the same meaning as commonly understood by one of ordinary skill in the art to which this invention belongs. Any preferred embodiment of the invention that will be described in connection with a particular aspect of the invention shall also apply to the other aspects of the invention. The plural forms also include the singular unless the context clearly dictates otherwise. All % is a weight percentage based on the total weight of composition, tablet, or capsule, unless stated otherwise.

The invention provides new and improved formulations of pharmaceutical drugs in solid dosage forms by direct compression or dry granulation. The invention is particularly suitable for preparing a compressed tablet form of moisture sensitive drugs. A useful application of the invention is to prepare a generic carglumic acid tablet of CARBAGLU.

CARBAGLU tablet is an orphan drug useful in treatment of hyperammonemia associated with N-acetylglutamate synthase deficiency. CARBAGLU tablet is presented as fast dissolving tablet containing 200 mg of carglumic acid as an API. Carglumic acid, also known as (2S)-2-(carbamoylamino)pentanedioic acid, is an amino acid derivative having both amino and carboxylic acid groups in its molecule. Carglumic acid is very hygroscopic and rapidly dissolvable in water.

According to one embodiment, a pharmaceutically acceptable carglumic acid formulation comprises about 30% w/w to about 50% w/w, preferably about 40% w/w, of carglumic acid, about 40% w/w to about 60% w/w of a cellulosic filler, and at least one lubricant, wherein no solvent or water is added or used in the formulation or process. Preferably, the inventive formulation has a pH greater than 3.5.

The cellulosic filler refers to any excipients or additives that are celluloses and the derivatives thereof. Typically, the cellulosic filler functions as a diluent or filler agent. As a filler/diluent, the cellulosic filler can impart satisfying compression characteristics to the formulation when it is present in sufficient quantity, and together with other excipients/additives. The cellulosic filler may also have anti-caking and binding functions. As a binder, the cellulosic filler imparts cohesiveness to a tablet formulation which insures the tablets remaining intact after compression as well as improving the free-flowing qualities of the formulation. The quantity of binder used has considerable influence on the characteristics of the compressed tablets. While too much binders may render the tablets too hard and not disintegrate easily, too little binders may not provide sufficient cohesiveness to the compressed tablets. One challenge of the present invention is that the binder is used in a dry form. It is known that the same amount of a binder in solution will be more effective than if it were dispersed in a dry form and moistened with the solvent. This is because in a dry form, the binding agent is not as effective in reaching and wetting each of the particles within the mass of the powders. However, the novel formulation of the present invention advantageously allows for a simpler and cost effective method of preparation, and at the same time produces rapidly disintegrated tablets.

In this invention, preferably, the excipients used in the formulation, including cellulosic fillers, lubricants, surfactants, glidants, and disintegrants, have pH more than 3.5 in which carglumic acid is stable. It is noticed that both batches of carglumic tablets are stable in an alkaline medium (pH 10) but undergo a rapid degradation in very acidic medium (pH 1). Thus preferably the cellulosic filler has a pH more than 3.5. The cellulosic filler can be selected from the group consisting of microcrystalline cellulose, hydroxypropyl methyl cellulose, croscarmellose sodium, silicified microcrystalline cellulose, carboxymethylcellulose, methylcellulose, powdered cellulose, hydroxyethyl cellulose, and combinations thereof. More preferably, the cellulosic filler consists of microcrystalline cellulose and hydroxypropyl methyl cellulose. Even more preferably, a USP grade of microcrystalline cellulose, Comprecel® M102, and a USP grade of hydroxypropylmethyl cellulose, Pharmacoat 603 are used in the composition. The formulation may comprise microcrystalline cellulose is in an amount of about 52.5% w/w and hydroxypropylmethyl cellulose in an amount of about 1.0% w/w.

Preferably, the at least one lubricant is sodium stearyl fumarate. In one embodiment, sodium stearyl fumarate in an amount of about 1.0% w/w is used in the composition. Lubricants are useful for improving the miscibility of the API and excipients. Lubricants have a number of functions in tablet manufacture. They improve the rate of flow of the tablet granulation, prevent adhesion of the tablet material to the surface of the dies and punches, reduced interparticle friction, and facilitate the ejection of the tablets from the die cavity. One major difficulty in the preparation of a water-soluble tablet is the selection of a satisfactory lubricant. Formulations used to prepare water-soluble tablets may represent a number of compromises between compression efficiency and water solubility. Other typical lubricants may also be used, for example, calcium stearate, magnesium stearate, stearic acid, talc, a vegetable oil, poloxamer, a mineral oil, sodium stearyl fumarate, zinc stearate, or combinations thereof.

The above inventive formulation may further comprise a disintegrant, a surfactant, a glidant, or combinations thereof.

Preferably, the glidant is in an amount of 0.3% w/w, the surfactant is in an amount of 0.2% w/w, and the disintegrant is in the amount of 5.0% w/w.

In one embodiment, croscarmellose sodium is used as a disintegrant. In a preferred embodiment, croscarmellose sodium with a tradename Disolcel® is used Croscarmellose sodium is an internally cross-linked sodium carboxymethylcellulose, often used as a super disintegrant in pharmaceutical formulations. A disintegrant facilitates the breakup of a tablet after administration or upon contact with water. Other disintegrants may also be used, such as povidone, crospovidone, carboxymethylcellulose, methylcellulose, alginic acid, sodium starch glycolate, starch, formaldehyde-casein, or their combinations.

A suitable glidant is anhydrous colloidal silicon dioxide. Anhydrous colloidal silicon dioxide provides good flowability to the composition. Its superiority resides in its uniform small particle size distribution with a very large specific surface area, which enables it to be uniformly distributed onto the surface of the dry-powder blend or dry granulates.

A suitable surfactant is sodium lauryl sulfate. Surfactants may improve disintegration of a tablet. It is believed that surfactants increase the rate of wetting upon contact with water or other liquid.

The formulation may utilize a dry granulation process or a direct compression process. The dosage forms of the inventive formulation may be either tablets or capsules.

According to another embodiment, a process for preparing pharmaceutical carglumic acid solid dosage forms comprising the steps of:
(1) mixing a composition comprising about 30 w/w % to about 50 w/w % of carglumic acid and about 40% w/w to about 60% w/w of a cellulosic filler to form a blend,
(2) mixing the blend from Step (1) with a lubricant, and
(3) forming a solid dosage form from the blend from Step (2),
wherein substantially no solvent or water is added in the process.

According to yet another embodiment, the above process can incorporate a dry granulation step by densifying the blend from Step (1) through slugging or passing the material between two counter-rotating rollers and breaking the resulting densified composition with a suitable milling technique following by sieving to collect a consistent particle size of the composition before proceeding to Step (2).

According to yet another embodiment, Step (2) is comprised of two steps: (2a) mixing the blend from Step (1) with a glidant and a surfactant; and (2b) mixing the blend from Step (2a) with the lubricant.

Carglumic acid, the cellulosic filler, the lubricant, the disintegrant, the glidant, and the surfactant may be sieved to obtain a desired particle size of each component, preferably through a 30 Mesh or smaller screen, prior to the mixing step. Optionally, they may be grounded prior to the sieving step.

According to a further embodiment, a compressed dosage form of a pharmaceutical composition is prepared by direct compression which comprises the steps of:
(1) dry mixing a composition consisting essentially of (a) at least one active pharmaceutical ingredient in an amount of from about 30.0% w/w to about 70.0% w/w, preferably, about 40% w/w, (b) microcrystalline cellulose in an amount of from about 30.0% w/w to about 75.0% w/w, preferably about 52.5% w/w, (c) croscarmellose sodium in an amount of from about 2% w/w to about 8% w/w, preferably about 5.0% w/w, and (d) hydroxypropylmethyl cellulose in an amount of from about 0.3% w/w to about 2.0% w/w, preferably about 1.0% w/w;
(2) dry mixing the dry-mix blend from Step (1) with anhydrous colloidal silicon dioxide in an amount of from about 0.1% w/w to about 1.0% w/w, preferably about 0.3% w/w, and sodium lauryl sulfate in an amount of from about 0.05% w/w to about 0.5% w/w, preferably about 0.2% w/w;
(3) dry mixing the dry-mix blend from Step (2) with sodium stearyl fumarate in an amount of from about 0.5% w/w to about 2.5% w/w, preferably about 1.0% w/w; and
(4) compressing the dry-mix blend from Step (3) to form a compressed tablet, or filling the dry-mix blend from Step (3) to capsules.

The components in Steps (1), (2), and (3) are typically mixed in a planetary mixer for a period of time until the mixture reaches uniform consistency. There is no particular order for adding the components within each of Steps (1), (2), and (3). Optionally, each of the components may be ground before being added to the planetary mixture. Alternatively, the components of each step are sieved so that a desired, uniformed particle size of each component is used for the mixing. The components may also be ground before being passing through the sieves. Different mesh sizes can be used to size the components. In a preferred embodiment, a sieve having a mesh size of 30 is used to screen the components in Step (1), a sieve having a mesh size of 40 is used to screen the components in Step (2), and a sieve having a mesh size of 60 is used to screen the components in Step (3).

The compressed tablets and filled capsules produced in Step (4) may contain a dosage unit strength from about 100 mg to 800 mg, preferably from about 200 mg to about 500 mg, and even more preferably, about 200 mg of the API per dosage unit.

Besides compression, tablets can also be made by molding, or by other accepted tablet forming methods. Compressed tablets are usually prepared by large-scale production methods while molded tablets often involve small-scale operations. The term "tablet" shall be understood to cover any kind of tablets, such as uncoated tablets, coated tablets, film-coated tablets, effervescent tablets, oral lyophilisates, orodispersable tablets, gastro-resistant tablets, prolonged-release tablets, modified-release tablets, chewable tablet, oral gums and pillules. The tablets can have an oblong form, a rectangle, circular shape, square-like or slightly oval or slightly rectangular shape. When preparing carglumic acid tablets, a 18×6 mm rectangle shaped punch is used to produce 18×6 mm rectangle tablets.

The compressed tablets or filled capsules are packed into a closed container, preferably a high density polypropylene container. For hygroscopic tablets or capsules, a desiccant unit is often included in the closed container. An example of the desiccant unit is silica gel. The packed bottles are then stored, preferably at a refrigerated temperature.

Compared to wet granulation, which necessarily involves the steps of binder preparation, wet mixing of powders and the binder, wet granulation, addition and removal of water and other liquids, the direct compression process is simple and efficient because less ingredients and less steps are involved. Additionally, the direct compression does not request an expensive wet granulation machines. A planetary mixer and a punch are essentially what are needed for the dry compression process. The dry-mix blends in accordance with the formulation of the present application possess sufficient flow characteristics and homogeneity for direct compression. They also have good compressing and filling characteristics. Sticking and filming on final compression punches and plunger faces are minimal even with minimal amounts of lubricants.

According to yet a further embodiment, a solid dosage form of a pharmaceutical composition is prepared by dry granulation which comprises the steps of:

(1) dry mixing a composition consisting essentially of (a) at least one active pharmaceutical ingredient in an amount of from about 30.0% w/w to about 70.0% w/w, preferably, about 40% w/w, (b) microcrystalline cellulose in an amount of from about 30.0% w/w to about 75.0% w/w, preferably about 52.5% w/w, (c) croscarmellose sodium in an amount of from about 2% w/w to about 8% w/w, preferably about 5.0% w/w, and (d) hydroxypropylmethyl cellulose in an amount of from about 0.3% w/w to about 2.0% w/w, preferably about 1.0% w/w;

(2) densifying the dry-mix blend from Step (1) by either slugging or passing the material between two counter-rotating rollers;

(3) crushing the resulting densified dry-mix blend from Step (2) followed by milling and/or sifting to form dry granules of an essentially uniform granule size;

(4) dry mixing the dry granules from Step (3) with anhydrous colloidal silicon dioxide in an amount of from about 0.1% w/w to about 1.0% w/w, preferably about 0.3% w/w, and sodium lauryl sulfate in an amount of from about 0.05% w/w to about 0.5% w/w, preferably about 0.2% w/w;

(5) dry mixing the dry-mix blend from Step (4) with sodium stearyl fumarate in an amount of from about 0.5% w/w to about 2.5% w/w, preferably about 1.0% w/w; and (6) compressing the dry-mix blend from Step (5) to form a compressed tablet, or filling the dry-mix blend from Step (5) to capsules.

The dry granulation process of the present invention may be performed in machinery and apparatus known to a person skilled in the art. During the dry granulation process, substantially no water or liquid is used. Similar to the direct compression process, in the dry granulation process, the components of each step may be sieved to obtain a desired particle size of each component. Optionally, the components may be grounded prior to the sieving. Different mesh sizes of sieves in one dry granulation process. Different types of punches can be employed to prepare compressed tablets of different sizes and shapes. Each solid dosage form unit contains about 100 mg to 800 mg, preferably from about 200 mg to about 500 mg, and even more preferably, about 200 mg of the API.

The dry granulation formulation of the invention allows the dry granulates to have a balanced level of hardness, density, particle size, and flow properties for final dosage formation. The problems commonly relate to a dry granulation process, such as non-homogeneity of the granulate mass, are not observed here. The resulting tablets prepared in accordance with the present invention are uniform and exhibit consistent physical properties.

Finding proper excipients for particular APIs, and finding a proper amount of each of the excipients and APIs, and determining the proper manufacturing process for the combination of excipients and APIs can be time-consuming. The formulations of the present invention are especially suitable for direct compression and dry granulation processes. It is believed that the particular compositions and the particular order to add and mix the components of the compositions are what contribute to the flowability, compressibility, and homogeneity of the bulk mass of the present invention. Moreover, the formulation of the present invention also contributes to the improved stability, dissolution, and other physical profiles of the solid dosage forms.

There are generally no limitations as to which APIs can be incorporated into the solid dosage forms of the invention. Any APIs, which have good compatibility with the excipients used in the formulation, may be prepared by the invention. The invention, however, is particularly suitable for making hygroscopic drugs (a.k.a. moisture sensitive drugs), as a result of eliminating water from the preparation process. Suitable APIs include, but are not limited to, hygroscopic APIs, acidic and basic APIs. Preferably, the API is carglumic acid.

A useful application of the present invention is the formulation of a generic CARBAGLU tablet. According to one embodiment, the carglumic acid tablet manufacturing process can be summarized as:

1) Direct compression method used to formulate high dose dispersible tablets.
2) Ingredients selected have pH more than 3.5, such as microcrystalline cellulose (Comprecel® M102), Croscarmellose sodium (Disolcel®), hydroxy propyl methyl cellulose 3 cps (Pharmacoat 603), anhydrous colloidal silicon dioxide, sodium lauryl sulfate and sodium stearyl fumarate.
3) Dispersible tablets are packed in high density polypropylene containers having 2 gm silica gel pillow pack and tightly closed by a polyethylene screw cap.

Example 1: By a Direct Compression Method

Procedure:

| Batch size: 1000 units | | | | |
|---|---|---|---|---|
| Sr. no. | Ingredients | mg/tablet | % w/w | Gm/batch |
| Dry-mix: | | | | |
| 1. | Carglumic acid | 200.00 | 40.00 | 200.00 |
| 2. | Microcrystalline cellulose (Comprecel ® M102) | 262.50 | 52.50 | 262.50 |
| 3. | Croscarmellose sodium (Disolcel ®) | 25.00 | 5.00 | 25.00 |
| 4. | Hydroxy propyl methyl cellulose (Pharmacoat 603) | 5.00 | 1.00 | 5.00 |
| Prelubrication: | | | | |
| 5. | Anhydrous colloidal silicon dioxide | 1.50 | 0.30 | 1.50 |
| 6. | Sodium lauryl sulfate | 1.00 | 0.20 | 1.00 |
| Lubrication: | | | | |
| 7. | Sodium stearyl fumarate | 5.00 | 1.00 | 1.00 |
| | Total weight: | 500.00 | 100.00 | 500.00 |

1. Dry-mix: Ingredient Nos. 1, 2, 3 and 4 are weighed accurately and passed through 30# sieve and mixed for 10 min in a planetary mixture.
2. Prelubrication: Take dry-mix blend from Step No. 1 and mix with anhydrous colloidal silicon dioxide and sodium lauryl sulfate (which already passed through 40# sieve) in a planetary mixture for 10 minutes.
3. Lubrication: Mix the Step No. 2 blend with sodium stearyl fumarate (already passed through 60# sieve) in a planetary mixture for 5 minutes.

4. Compression: Compress the tablets using 18×6 mm rectangle shaped punches.
5. Packaging: Dispersible tablets are packed in high density polypropylene containers having 2 gm silica gel pillow pack and tightly closed by a polyethylene screw cap.

It is noticed that the lubricated blend for direct compression exhibit good flow property and satisfied compression parameters. There is no weight variation occurred during the direct compression process.

Example 2: By Wet Granulation Method (a Prior Art Method)

Batch size: 1000 units

| Sr. No. | Ingredients | mg/tablet | % w/w | Gm/batch |
|---|---|---|---|---|
| | Dry-mix: | | | |
| 1. | Carglumic acid | 200.00 | 40.00 | 200.00 |
| 2. | Microcrystalline cellulose (Comprecel ® M101) | 262.50 | 52.50 | 262.50 |
| 3. | Croscarmellose sodium (Disolcel ®) | 12.50 | 2.50 | 12.50 |
| | Binder preparation: | | | |
| 4. | Hydroxy propyl methyl cellulose 3 cps (Pharmacoat 603) | 5.00 | 1.00 | 5.00 |
| 5. | Sodium lauryl sulfate | 1.00 | 0.20 | 1.00 |
| 6. | Purified water* | Q.S. | — | 150 |
| | Prelubrication: | | | |
| 7. | Croscarmellose sodium (Disolcel ®) | 12.50 | 2.50 | 12.50 |
| 8. | Anhydrous colloidal silicon dioxide | 1.5 | 0.30 | 1.5 |
| | Lubrication: | | | |
| 9. | Sodium stearyl fumarate | 5.00 | 1.00 | 5.00 |
| | Total weight: | 500.00 | 100.00 | 500.00 |

*Purified water is used in manufacturing process only, but it does not appear in the final product.

Procedure:
1. Dry-mix: Ingredient Nos. 1, 2 and 3 are weighed accurately and passed through 30# sieve. Mix them in a planetary mixture for 10 minutes.
2. Preparation of binder solution: Ingredient Nos. 4 and 5 are weighed accurately and dissolved in appropriate quantity of purified water.
3. Wet granulation: Step No. 1 blend granulate with Step No. 2 binder solution in a planetary mixture.
4. Drying and Sizing: Drying is performed in a fluid bed dryer until loss on drying ("LOD") no more than 2% w/w is achieved at 105° C. on a Halogen moisture analyzer. Dried granules are passed through 20# sieve.
5. Prelubrication: Dried granules from Step No. 3 and ingredient No. 7 & 8 (Previously passed through 30# sieve) are mixed in a planetary mixture for 10 minutes.
6. Lubrication: The blend from Step No. 4 and ingredient No. 9 (passed through 60# sieve) are mixed in a planetary mixture for 5 minutes.
7. Compression: Compress the tablets using 18×6 mm rectangle shaped punches.
8. Packaging: Dispersible tablets are packed in high density polypropylene containers having 2 gm silica gel pillow pack and tightly closed by a polyethylene screw cap.

While the wet granulation process provides reasonably good flow properties and satisfied compression parameters, the granulates are sticking to the punches and planetary mixtures. In contrast, none of the issues are observed in the direct compression method.

Evaluation of Tablet Properties:

Both batches of carglumic acid tablets from Examples 1 and 2 are evaluated using USP 35/NF 30 (2013) and by non pharmacopoeial tests, the results are shown in Table 1.

TABLE 1

Evaluation of Tablet Properties

| Sr. No. | Test | Example 1 (Direct compression) | Example 2 (Wet granulation) |
|---|---|---|---|
| 1. | Average weight (mg) | 500.00 | 500.00 |
| 2. | Thickness (mm) | 4.85-4.92 | 4.81-4.92 |
| 3. | Hardness (kg) | 12-14 | 11-13 |
| 4. | Disintegration time (sec) | 15-20 | 35-36 |
| 5. | Friability in % w/w | 0.120 | 0.060 |
| 6. | Assay % | 100.87 | 103.17 |

The above comparison in Table 1 shows that, the carglumic acid tablet made by the direct compression method has comparable physiological and chemical properties of CARBAGLU tablet (i.e., made by wet granulation), yet it has an improved disintegration profile. Significantly, the tablet can be disintegrated within 15-20 seconds upon contact with water, which is an improvement to the tablet made by wet granulation, which disintegrates after 30 seconds upon contact with water in the comparative study.

Both batches of carglumic acid tablets from Examples 1 and 2 are also evaluated for stability under stress conditions. It is noticed that both batches of carglumic tablets are stable in an alkaline medium (pH 10) but undergo a rapid degradation in very acidic medium (pH 1). The referenced listed drug tablets (i.e., CARBAGLU tablet) and tested products have pH 2.50 and 2.88 respectively.

Carglumic acid is slowly degraded when exposed to light or an oxidizing medium such as hydrogen peroxide. Principal degradation products are hydantoin-5-propionic acid ("5-HPA") and diaza-1,3-dione-2,4-carboxy-7-cycloheptane. Among them, 5-HPA is toxic and thus it must be controlled below 0.1%. L-Pyroglutamic acid is another common impurity in the carglumic acid tablet.

Table 2 shows accelerated stability testing results after subjecting both batches under a stressed condition, at 50° C. up to 21 days, which equals to approximately one year at room temperature. The carglumic acid tablets are packed and sealed in a 75 mL HDPE bottle with 2 gm of silica gel in the bottle, and then subjected to the stressed condition.

TABLE 2

Stability Data at 50° C.

| | Test Batch No. | | | |
|---|---|---|---|---|
| | Trial 1 (Direct compression) | | Trial 2 (Wet granulation) | |
| | Initial | 21 Days 50° C. | Initial | 21 Days 50° C. |
| API % | 100.87 | 99.39 | 103.17 | 104.23 |
| Impurity.at RRT (min.) | | | | |
| 1.34 | ND | ND | ND | 0.013 |
| 1.88 (5-HPA) | 0.002 | 0.009 | 0.08 | 0.673 |

TABLE 2-continued

Stability Data at 50° C.

| | Test Batch No. | | | |
|---|---|---|---|---|
| | Trial 1 (Direct compression) | | Trial 2 (Wet granulation) | |
| | Initial | 21 Days 50° C. | Initial | 21 Days 50° C. |
| 2.06 | ND | ND | 0.030 | 0.025 |
| 2.14 | 0.024 | 0.027 | ND | ND |
| 2.40 | ND | ND | 0.037 | ND |
| 2.53 | 0.035 | 0.040 | ND | 0.310 |
| 3.38 | 0.007 | 0.018 | ND | 0.013 |
| 4.06 | 0.042 | 0.045 | 0.055 | 0.059 |
| 4.09 | ND | 0.012 | 0.010 | 0.010 |
| Total Impurities | 0.111 | 0.151 | 0.141 | 1.102 |

In Table 2, the API and impurities are measured by High Performance Liquid Chromatography ("HPLC") using N-Carbamoyl-L-glutamic acid as a standard under the following conditions:

| Column | T3 |
|---|---|
| | (250 × 4.6 mm, 5.0 μm) |
| Flow rate | 1.0 mL/min |
| Wavelength of the detector | 205 nm |
| Column temperature | 25.0° C. |
| Sample cooler temperature | 5.0° C. |
| Injection volume | 50 μL |
| Run time | 70 mins |
| Rinsing solvent | Water |

The solvent system of the HPLC analysis is a gradient system, as shown in Table 3:

TABLE 3

HPLC Gradient Condition

| Time (min) | % Mobile phase A | % Mobile phase B |
|---|---|---|
| Initial | 100 | 0 |
| 55 | 90 | 10 |
| 60 | 100 | 0 |
| 70 | 100 | 0 |

The mobile phase A is a potassium dihydrogen orthophosphate aqueous solution which has pH 2.5. The mobile phase A is prepared as follows: weigh 2.72 g of potassium dihydrogen orthophosphate and transfer it into a suitable container, add 1,000 mL of water, sonicate to dissolve into an aqueous solution, then adjust the aqueous solution to pH 2.5 using orthophosphoric acid, followed by mixing and filtering through 0.2 μm membrane filter. The mobile phase B is a mixture of methanol and the mobile phase A in the ratio of 95:5. After mixing methanol and the mobile phase A, the mobile phase B is degassed before use.

Table 2, Trial 1, shows that the impurity level of the generic carglumic acid tablets prepared by direct compression does not increase as much when compared to the initial impurity level, from 0.151% to 0.111%. Importantly, the level of the toxic degradation product, 5-HPA, is 0.009% after 21 days at 50° C., which is much below the control level of 0.1%.

In contrast, the impurity level of the carglumic acid tablets prepared by wet granulation (i.e., the method used to prepare the commercial tablets) exhibits a significant increase, from 0.141% to 1.102%, as shown in Table 2, Trial 2. The level of the toxic degradation product, 5-HPA, increases from the initial 0.08% to 0.673% after 21 days at 50° C., which is much higher than the control level of 0.1%. Thus, the carglumic acid tablets are no longer unsuitable for drug administration. This stability profile is consistent with the stability of the commercial tablets, which are made by wet granulation. The package insert of the commercial tablets, CARBUGLU, requires that the tablets be stored refrigerated. Moreover, it states that an opened bottle should be stored at room temperature and that any remaining tablets in a bottle one month after the bottle opens must by discarded. In other words, the commercial CARBUGLU tablet is not stable.

Table 4 shows another set of accelerated stability testing results after subjecting the carglumic acid tablets prepared in accordance with the present invention at 40° C., 75% RH ("relative humidity"). The carglumic acid tablets are packed and sealed in a 75 mL HDPE bottle with 2 gm of silica gel in the bottle, and then subjected to the stressed condition at 40° C., 75% RH for up to six months. In Table 4, the API and impurities are measured using the same HPLC conditions as used in Table 2.

TABLE 4

Stability Data at 40° C.

| | Initial | 1 months | 2 months | 3 months | 6 months |
|---|---|---|---|---|---|
| Assay % | 100.8 | 99.97 | 99.27 | 98.68 | 98.15 |
| Impurity at RRT (min.) | | | | | |
| 1.34 | ND | ND | ND | ND | ND |
| 1.88 (5-HPA) | 0.001 | 0.009 | 0.015 | 0.022 | 0.027 |
| 2.11 | 0.024 | 0.045 | 0.030 | 0.022 | 0.028 |
| 2.4 | ND | ND | ND | 0.001 | 0.002 |
| 2.52 | 0.014 | 0.031 | 0.019 | ND | ND |
| 3.24 | ND | ND | ND | 0.018 | 0.019 |
| 3.39 | 0.016 | 0.013 | 0.017 | ND | ND |
| 4.00 | 0.027 | 0.025 | 0.029 | ND | ND |
| 4.02 | ND | 0.007 | 0.009 | | |
| 5.52 | ND | ND | ND | 0.029 | 0.024 |
| 5.70 | ND | ND | ND | 0.006 | 0.006 |
| Total Impurities | 0.083 | 0.130 | 0.120 | 0.098 | 0.106 |

Table 5 shows the stability testing results after subjecting the carglumic acid tablets prepared in accordance with the present invention at room temperature for six months. The carglumic acid tablets are packed and sealed in a 75 mL HDPE bottle with 2 gm of silica gel in the bottle, and then stored at room temperature, 60% RH. In Table 5, the API and impurities are measured using the same HPLC conditions as used in Table 2.

TABLE 5

Stability data at room temperature Up to 6 months

| | Initial | 3 months | 6 months |
|---|---|---|---|
| Assay % | 100.8 | 99.60 | 97.86 |
| Impurity. at RRT (min.) | | | |
| 1.34 | | ND | ND | ND |
| 1.88 (5-HPA) | 0.001 | 0.008 | 0.013 |

TABLE 5-continued

Stability data at room temperature Up to 6 months

|  | Initial | 3 months | 6 months |
|---|---|---|---|
| 2.11 | 0.024 | 0.022 | 0.013 |
| 2.4 | ND | 0.001 | 0.001 |
| 2.52 | 0.014 | ND | ND |
| 3.24 | ND | 0.019 | 0.023 |
| 3.39 | 0.016 | ND | ND |
| 4.00 | 0.027 | ND | ND |
| 5.52 | ND | 0.025 | 0.025 |
| 5.70 | ND | 0.007 | 0.008 |
| Total Impurities | 0.083 | 0.081 | 0.088 |

As shown in Table 5, the level of the impurity, 5-HPA, in the tablets increases from the initial 0.001% to 0.008% after the tablets are stored at room temperature for 3 months, and further to 0.013% after the tablets are stored at room temperature for 6 months. In each case, the level of 5-HPA is much lower than the control level of 0.1%. The total impurities level is 0.088% after 6 months storage at room temperature, which meets the typical requirement that total impurities level of less than 0.1% for a pharmaceutical drug.

To summarize, using direct compression or dry granulation process to prepare generic carglumic acid tablets is simpler and more cost effective because the process involves fewer and simpler steps than that of wet granulation. It uses less components for the process and also avoids the issues typically associated with wet granulation. Table 1 shows that the carglumic acid tablets prepared by direct compression or dry granulation process show an improved disintegration rate compared the commercial CARBAGLU tablet. From the stability testing results in Tables 2, 4 and 5, it is apparent that the carglumic acid tablets prepared by direct compression or dry granulation are more stable and show better stability profiles under both stressed and normal conditions than the commercial CARBAGLU tablet. It is known that CARBAGLU tablet must be stored refrigerated and can be only stable at room temperature for about one month. In contrast, the present invention provides the carglumic tablets that are stable for at least six months at room temperature. The improved stability is probably due to the fact the inventive formulation and process avoids the oven drying step in the wet granulation process in which carglumic acid and the excipients are subjected to a high temperature and thereby CARBAGLU tablet is more prone to degradation.

According to the present invention, a fast dissolving carglumic acid dispersible tablet is formulated by direct compression or dry granulation method. Direct compression and dry granulation methods reduce the formulation steps of wet granulation method, such as binder preparation, granulation, drying and sizing of drug granules, which ultimately reduce the manufacturing cost of formulation. They also avoid the technical issues commonly associated with wet granulation as described in the background of this application. Overall, the processes of the prevent invention in manufacturing carglumic acid tablets is cost effective and easy.

The above description is provided for the purpose of describing embodiments of the invention and is not intended to limit the scope of the invention in any way. It will be apparent to those skilled in the art that various modifications and variations can be made without departing from the spirit or scope of the invention. Thus, it is intended that the present invention cover the modifications and variations of the invention provided they come within the scope of the appended claims and their equivalents.

What is claimed is:

1. A process for preparing a pharmaceutical carglumic acid tablet comprising the steps of:
   (1) dry mixing a composition comprising about 30 w/w % to about 50 w/w % of carglumic acid and about 40% w/w to about 60% w/w of a cellulosic filler to form a blend,
      wherein the cellulosic filler is selected from a group consisting of microcrystalline cellulose, hydroxypropyl methyl cellulose, croscarmellose sodium, silicified microcrystalline cellulose, carboxymethylcellulose, methylcellulose, powdered cellulose, hydroxyethyl cellulose, and combinations thereof;
   (2) dry mixing the blend from Step (1) with about 0.5% to about 2.5% by weight of a lubricant;
   (3) compressing the blend from Step (2) to form a tablet; and
   (4) sealing the tablet in a container with a dessicant unit, wherein the tablet contains at least an order of magnitude less hydantoin-5-propionic acid than a comparable tablet produced by wet granulation after each tablet is stored in a sealed container having desiccant at a temperature of 50° C. for 21 days.

2. The process of claim 1, further comprising the steps of:
   densifying the mix blend from Step (1) by slugging or passing the blend between two counter-rotating rollers, milling, and sieving the densified blend, before conducting Step (2).

3. The process of claim 1, further comprising the step of grinding each of carglumic acid, the cellulosic filler, the lubricant, and optionally a disintegrant and a surfactant, prior to Steps (1) and (2).

4. The process of claim 1, further comprising the step of sieving each of carglumic acid, the cellulosic filler, the lubricant and, optionally a disintegrant and a surfactant, through a 30 Mesh or smaller screen prior to Steps (1) and (2).

5. The process of claim 1, wherein the cellulosic filler is microcrystalline cellulose, hydroxypropyl methyl cellulose, and croscarmellose sodium.

6. The process of claim 1, wherein Step (2) is comprised of the following sub-steps:
   (2a) mixing the blend from Step (1) with a glidant and a surfactant; and
   (2b) mixing the blend from Step (2a) with the lubricant.

7. A pharmaceutically acceptable carglumic acid tablet prepared according to claim 6,
   wherein in Step (1) carglumic acid is 40% w/w, microcrystalline cellulose is 52.5% w/w, croscarmellose sodium is 5.0% w/w, and hydroxypropylmethyl cellulose is 1.0% w/w;
   wherein in Step (2a) the glidant is colloidal silicon dioxide in an amount of 0.3% w/w and the surfactant is sodium lauryl sulfate in an amount of 0.2% w/w, and
   wherein in Step (2b) the lubricant is sodium stearyl fumarate in an amount of 1.0% w/w.

8. A process for preparing a pharmaceutically acceptable carglumic acid direct compression tablet comprising the steps of:
   (1) dry mixing a composition consisting essentially of carglumic acid in an amount of from about 30.0 to about 70.0% by weight of the tablet, microcrystalline cellulose in an amount of from about 30.0 to about 75.0% by weight of the tablet, croscarmellose sodium in an amount of from about 2% w/w to about 8% by weight of the tablet, and hydroxypropylmethyl cellulose in an amount of from about 0.3% to about 2.0%, by weight of the tablet;

(2) dry mixing the blend from Step (1) with anhydrous colloidal silicon dioxide in an amount of from about 0.1% to about 1.0% by weight of the tablet and sodium lauryl sulfate in an amount of from about 0.05% w/w to about 0.5% w/w by weight of the tablet;

(3) dry mixing the blend from Step (2) with sodium stearyl fumarate in an amount of from about 0.5% to about 2.5% by weight of the tablet;

(4) compressing the blend from Step (3) to form a tablet; and (5) sealing the tablet in a container with a dessicant unit, wherein the tablet contains at least an order of magnitude less hydantoin-5-propionic acid than a comparable tablet produced by wet granulation after each tablet is stored in a sealed container having desiccant at a temperature of 50° C. for 21 days.

9. A pharmaceutically acceptable carglumic acid tablet prepared according to claim 8, wherein the tablet disintegrates within 20 seconds upon contact with water.

* * * * *